United States Patent [19]

Curry et al.

[11] Patent Number: 4,679,939
[45] Date of Patent: Jul. 14, 1987

[54] IN SITU SMALL PARTICLE DIAGNOSTICS

[75] Inventors: Bill P. Curry, Dechard; John H. Jones, Shelbyville; Brian L. Seiber; Lynwood L. Price, both of Tullahoma; Homer M. Powell, Auburntown; Earl L. Kiech, Tullahoma, all of Tenn.

[73] Assignee: The United States of America as represented by the Secretary of the Air Firce, Washington, D.C.

[21] Appl. No.: 812,206

[22] Filed: Dec. 23, 1985

[51] Int. Cl.$^4$ ..................... G01N 15/02; G01N 21/53
[52] U.S. Cl. .................................. 356/336; 356/339
[58] Field of Search .................. 356/336, 338, 339; 250/564, 574

[56] References Cited

U.S. PATENT DOCUMENTS

| | | | |
|---|---|---|---|
| 3,612,689 | 11/1968 | Liskowitz | 356/103 |
| 3,653,767 | 4/1972 | Liskowitz | 356/336 |
| 3,871,769 | 3/1975 | Engel et al. | 356/102 |
| 3,901,602 | 8/1975 | Gravatt, Jr. | 356/114 |
| 4,053,229 | 10/1977 | McCluney | 356/103 |
| 4,118,625 | 10/1978 | Underwood | 250/343 |
| 4,140,902 | 2/1979 | Young | 356/339 X |
| 4,338,030 | 7/1982 | Loos | 356/336 |

OTHER PUBLICATIONS

T. Prosch, D. Hennings, and E. Raschke, "Video Polarimetry: A New Imaging Technique in Atmospheric Science", Applied Optics, May 1, 1983.
B. Curry, D. Weaver, and J. Lewis, "Time and Space Dependence of Particulate Effluent in the Exhaust Plume of a Pulsed Liquid Bipropellant Engine", AEDC-TR-80-44, Oct. 1981.
B. Curry, D. Weaver, and J. Lewis, "Development of MIE Scattering Techniques for in situ Particle Diagnostics at AEDC", AEDC-TR-80-3, Nov. 1980.
W. D. Williams, H. M. Powell, J. H. Jones, and R. L. McGuire, "Multichannel Detection Systems Available for Flow Diagnostics at AEDC", AEDC-TR-83-28, Aug. 1983.

Primary Examiner—Davis L. Willis
Assistant Examiner—Matthew W. Koren
Attorney, Agent, or Firm—Gerald B. Hollins; Donald J. Singer

[57] ABSTRACT

Small particle diagnostic apparatus employing illumination by coherent light of high polarization ratio, polarized separation of the reflected particle scatter optical signals and the ability to consider particles in plural locations of a diagnostic aperture aided by use of a vidicon or other position-sensitive transducer device and an optional image intensifier device. Digital storage and analysis of the particle scatter data and computer control of the optical and analysis sequences are contemplated.

35 Claims, 5 Drawing Figures

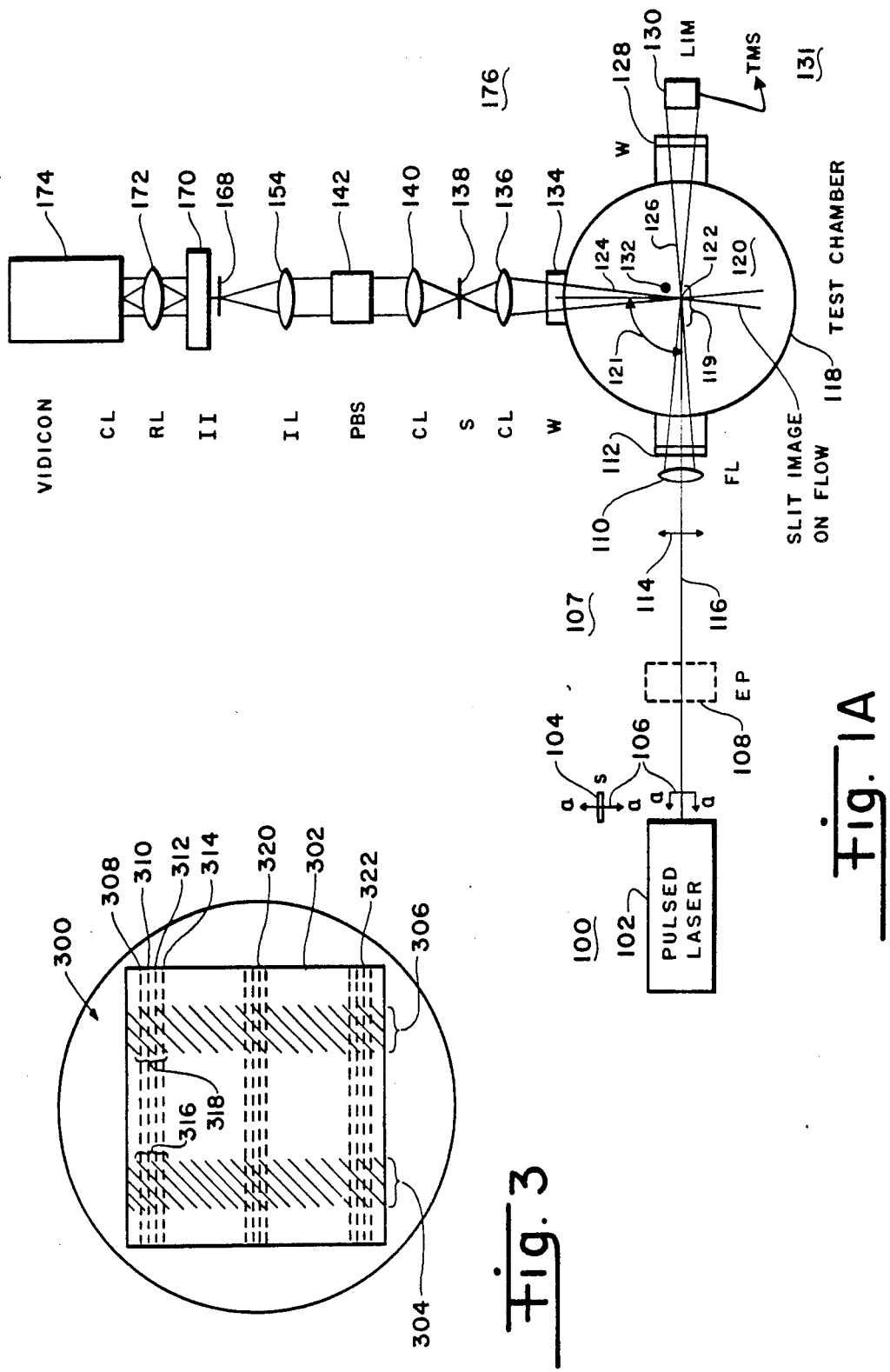

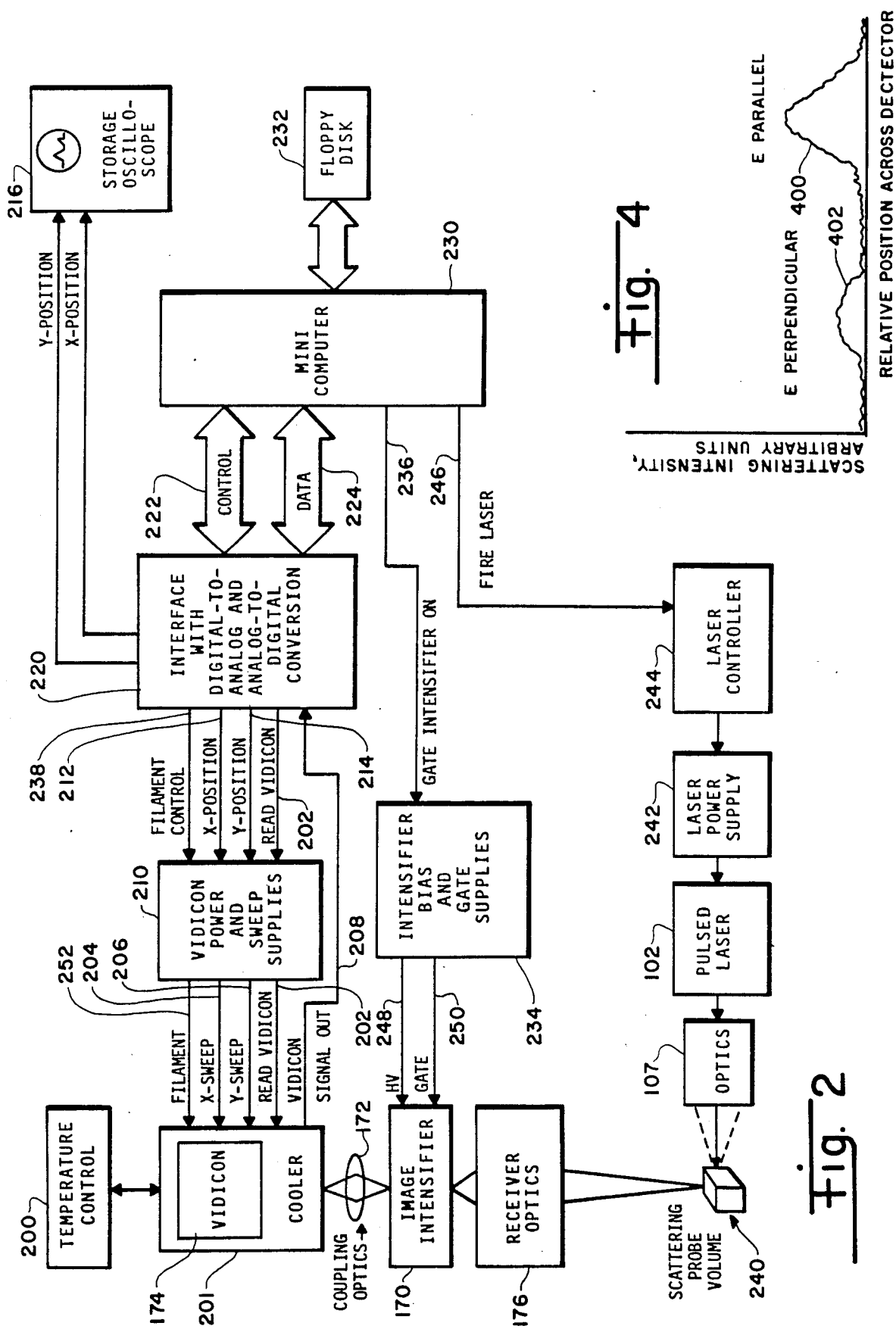

IN SITU SMALL PARTICLE DIAGNOSTICS

RIGHTS OF THE GOVERNMENT

The invention described herein may be manufactured and used by or for the Government of the United States for all governmental purposes without the payment of any royalty.

BACKGROUND OF THE INVENTION

This invention relates to the field of small particle size measurement and particle size distibution determinations in a stream of moving particles.

In numerous fields of current technical interest it is desirable to know the physical characteristics of small particles which are dispersed in a medium such as air or vacuum. Particle populations of this type may be of concern, for example, when liquids under pressure are ejected into the vacuum of outer space, or when air of imperfect purity is considered—especially at high velocity, as in a wind tunnel, or in the case of an aircraft moving through the atmosphere, or in the products of combustion of hydrocarbon fuels. Such particles can also be of concern in the gas and moisture exchange processes employed by living organic specimens, such as in human breathing, in the discharge of propelled projectile weapons, and in a diversity of other phenomena now under quantitative technical investigation.

Often the particles encountered in these applications have diameters of a few microns or a fraction of a micron and are therefore viewed or subjected to precise analysis only with carefully considered apparatus and techniques. The use of light scattered by small particles as a basis for observation and defining particle characteristics is well known in this art, and the mathematics relating to particle characterizations has been developed by workers such as Rayleigh, Lorenz, and Mie. The terms "Reyleigh scattering" and "Mie scattering" are commonly used in the diagnosis of particles residing in well-defined size and property classes. It is notable, however, that none of this prior particle diagnostic work has afforded the capability of analyzing particles existing in plural locations of a particle population through the use of coherent light excitation and polarized segregation of the particle scattered light into optical signal components.

The patent art, as is characterized by several patents in the particle diagnostic field, illustrates the absence of multiple point bipolar partial analysis capability. This patent art does include, however, several examples of particle measuring and size distribution apparatus. One example of such apparatus is found in the patent of Andreas H. Engel, U.S. Pat. No. 3,871,769, which discloses an apparatus for determining the diameters of small particles. The Engel apparatus is based on the use of coherent laser supplied light, a plurality of reflecting hologram filters which may employ the concept of Mie's scattering theory and a plurality of optical-to-electrical transducer detectors. In the Engel invention, laser light is focused at a plurality of physically separated focal points located along the axis of a Fresnel lens apparatus and particles of successively different size are detected at each of the successive focal points. In the Engel apparatus a good degree of agreement between the diameter of particles under consideration and the diameter contemplated in fabricating the respective light filter elements results in the generation of spherically shaped patterns which pass through a predetermined aperture with little loss; this situation is contrasted with a condition of disagreement between the filter and particle size wherein the light waves pass through the predetermined aperture with great loss of energy. The Engel invention is therefore based on the concept of identifying agreement between predetermined filter elements and the light waves resulting from a particle diffusion event. The Engel invention, further, must size a single particle at a time.

Another particle measurement apparatus, one intended for measuring particle size distributions, is shown in the patent of Hendricas G. Loos, U.S. Pat. No. 4,338,030, wherein the use of an array of different filter elements for again seeking a condition of match between filter characteristics and the particle size related diffusion of incident light energy is accomplished. The Loos apparatus employs a pulsed light source of preferably collimated white polarized light, uses a polarizer, and is arranged to seek a maximum light transfer through a filter which has a transmittance pattern precisely matching the Mie pattern of the incoming light. From the match between the Mie pattern and the filter characteristics, particle or drop size can be inferred. The Loos apparatus also contemplates the unraveling or separation of contributions by the Mie patterns belonging to different drop size classes.

Another particle measuring apparatus is shown in the patent of W.B. Underwood, U.S. Pat. No. 4,118,625, which concerns a nephelometer having a pulsed source of energy, preferably a pulse driven solid state laser device. The Underwood patent indicates a nephelometer to be a device wherein a beam of light traverses a liquid or other fluid for the purpose of detecting and measuring the scattering function of particles suspended in the fluid. The Underwood particle apparatus contemplates the use of infrared frequency energy and the use of a detector arrangement capable of ignoring ambient light conditions by way of pulsing the infrared energy of interest in performing the particle measurements.

A photometer for measuring the light scattered by particles in a hydrosol is disclosed in the patent of William R. McCluney, U.S. Pat. No. 4,053,229, which is entitled "2°/90° Laboratory Scattering Photometer". The McCluney apparatus is intended for use in distinguishing between particles of high index of refraction with respect to water such as silica or calcium carbonate or other inorganic materials (and including organic skeletal materials, such as bone), and particles having a low index of refraction relative to water, such as organic tissue material—material wherein the light scattering ability tends to be at angles greater than 80° on the one hand, and at angles of 1° to 10° on the other hand. The McCluney apparatus is further arranged to be convenient for use on vessels traveling in natural waters and industrial streams for performing a continuous particle analysis while the vessel is in motion. The McCluney apparatus also includes a beam splitting device which is used for monitoring the performance of the laser light source and employs photoelectric transducers that are preferably of the silicon diode rather than scanning or imaging type.

SUMMARY OF THE INVENTION

An object of the present invention is to provide an improved particle diagnostic apparatus capable of responding to low and moderate density particle streams which include particles of micron and submicron size.

Another object of the invention is to provide particle diagnostic apparatus capable of sensing particle characteristics in plural locations of a moving particle stream.

Another object of the invention is to provide a plural stream location particle diagnostic apparatus which employs polarized separation of particle scattering light signals.

Another object of the invention is to provide a particle diagnostic apparatus which employs scanned sensing of polarized images originating in plural locations of a particle sample.

Another object of the invention is to provide a particle diagnostic apparatus capable of optimally responding to particles of different size.

Another object of the invention is to provide a particle diagnostic apparatus which realizes the benefit of excitation by highly polarized optical energy.

Another object of the invention is to provide a particle diagnostic apparatus capable of indicating both particle density and particle size distribution parameters at plural locations of a particle stream.

Additional objects and features of the invention will be understood from the following description and the accompanying drawings.

These objects are achieved by a moving particle stream diagnosis signal generating apparatus which includes laser means for illuminating a cross-section of the particle stream with coherent polarized light directed along a lateral axis transverse of the cross-section, means located at a predetermined angle with respect to the cross-section lateral axis and the stream for collecting the particle scattered light originating in plural locations of the illuminated cross-section into first optical signals; means for segregating the first light signals into a second and third signal pair of component optical signals of orthogonal polarization vectors; means for dispersing the second and third component optical signals over a common image plane, the image plane receiving a second and third optical signal pair for each said cross-section location first optical signal; and means for transducing the second and third optical signal pairs into electrical signal pairs.

BRIEF DESCRIPTION OF THE DRAWINGS

FIG. 1A is a schematic diagram of a particle diagnostic apparatus capable of multiple stream locus polarized light particle diagnosis.

FIG. 2 shows a block diagram of electrical apparatus used with the FIG. 1A and 1B optical components.

FIG. 3 is a representation of the optical signals produced by the FIG. 1A and 1B apparatus.

FIG. 4 shows amplitude relationships for two signals of the FIG. 3 type.

DETAILED DESCRIPTION

Figure 1B:
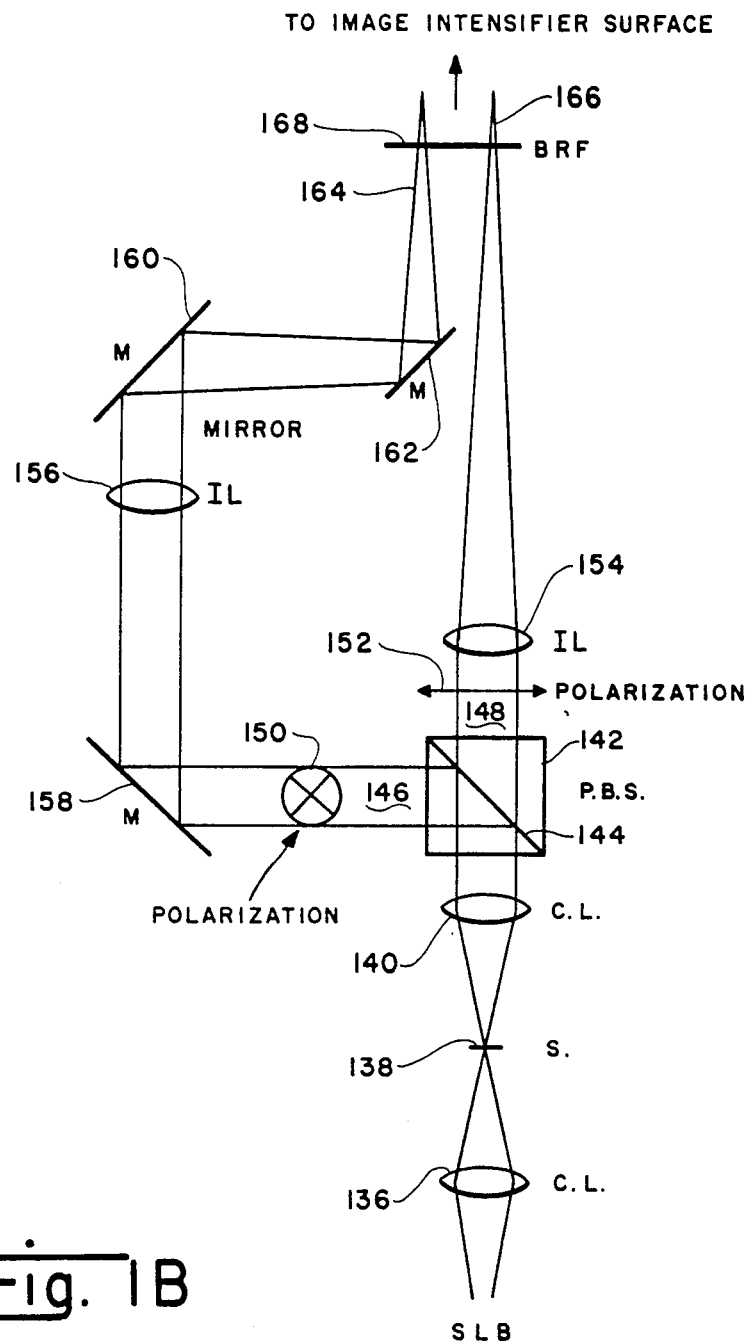
FIG. 1B shows additional details of parts of the optical imaging apparatus in FIG. 1A.

In FIG. 1A of the drawings, there is shown a schematic diagram of the optical elements in a small particle diagnostic apparatus capable of providing quantitative data about particles in multiple points of a particle stream sample window. The FIG. 1A apparatus includes a source of illumination 100, a particle flow chamber 120, and particle signal analyzing apparatus 176; each of these major portions in FIG. 1A includes a number of component elements which are shown in detail in FIG. 1A and 1B and described below.

The illumination source 100 in FIG. 1A provides high intensity coherent light; this source is moreover capable of providing coherent light with a high degree of polarization that is, for example, laser light having a large ratio of amplitudes between the vertically polarized components and the horizontally polarized components of the output beam. Such a laser as indicated at 102 in FIG. 1A, is preferably of the pulsed type, and desirably provides illumination levels of 100 millijoules per output pulse at a wavelength in the region of three hundred eight nanometers. The laser used in the FIG. 1A apparatus should, specifically, be vertically polarized and have a vertical-to-horizontal polarization ratio that is above thirty-five to one and desirably in the range of 100:1 or greater. A polarization ratio of even 1000:1 is beneficial for this laser but of somewhat difficult realization according to the present state of the laser art. The laser preferred for use in the FIG. 1 apparatus is of the excimer, excited dimer type, the word "excimer" being a contraction of the words "excited" and "dimer". Lasers of this type usually employ a noble gas such as xenon which is doped with a suitable impurity gas, such as chlorine, for example, or alternately, may employ krypton containing a fluorine dopant. Although other noble gases including argon and other dopant materials can be employed in the laser 102, the xenon-chloride laser provides desirable near-ultraviolet spectrum optical energy output. This near-UV energy is released in pulses of 10 to 20 nanoseconds duration each in the desired laser. In addition to the argon and krypton gaseous lasers, the ruby laser used in a frequency doubling arrangement might also be employed in the FIG. 1A apparatus, with illumination wavelengths which differ slightly from the indicated 308 nanometers.

Laser output wavelengths near 308 nanometers are preferable for diagnosis of particles in the submicron diameter range. For supermicron particles, longer wavelengths in the visible region of the spectrum are desirable, and these wavelengths can be provided either by using the excimer laser to pump a dye laser having tunable visible wavelength output or by using a separate visible laser system. The slit arrangement indicated at 104 restricts the laser output to a well defined beam of rectangular cross-section. The slit 138 in the scattered energy path similarly restrics the detected scattered light to a rectangular region whose long axis is transverse to the flow axis. Thus, these two slits, together with associated lenses, define a doubly rectangular shaped focal volume containing the particles whose scattered light will be detected.

The optical energy flowing along the path 116 between the laser 102 and the particle flow chamber 120 is preferably of a coherent and highly intrinsic polarized nature—as described above the amplitude of the vertical and horizontal polarization components in this light should have ratios in the order of 100:1 to 1000:1 and at least 98:1. Since intrinsic polarization ratios of this degree are difficult to achieve within some laser devices, the use of an external polarizer as indicated at 108, may be desirable. A polarizer suitable for use at 108 in FIG. 1A can be fabricated from a stack of quartz windows mounted at successive Brewster's angle rotational positions with respect to each other. A stack of six such quartz windows has been found suitable for use as an external polarizer with FIG. 1A type embodiments of the present apparatus. For wavelengths longer than 308 nanometers, commercial polarizers are available.

The initials EP are used in FIG. 1A to identify the external polarizer 108; abbreviations of the common name for other elements in the FIG. 1A apparatus are also shown in the drawings in addition to the more formal numerical designations. Use of these name abbreviations simplifies association of the elements in the FIG. 1A apparatus with description names as an aid to comprehension of the invention description.

In describing the present invention, it is presumed that the particles of analysis interest are moving within a particle flow chamber 120, which can be an evacuated chamber to, for example, simulate conditions existing in free space. The chamber 120, for an additional example, might be an evacuated chamber into which pulses of water in finely divided form are introduced—in simulation of the events occurring when liquids are ejected under pressure from a spacecraft. Flow of the particles in the chamber 120 is indicated by the dot 132 which is depicted in accordance with the convention that flow out of the plane of the FIG. 1A drawing might be represented by the head of an arrow or a dot, while flow into the plane of the FIG. 1A drawing might be represented by a circle indicating the tail of an arrow.

The chamber 120 in FIG. 1A can be in the form of a sphere or an elongated cylinder having an outer periphery 118 that is interrupted by three window aperture structures 112, 128, and 134. These window apertures are capable of transmitting optical energy while maintaining the evacuated or otherwise pressurized environment desired within the chamber. The window aperture structure 112 which admits the optical energy flowing along the path 116 is shown to include a focusing lens 110 capable of converging the energy received along the path 116 onto a small laterally-elongated window region across the particle flow path as indicated at 119.

Optical energy received along the path 116 divides into two portions 124 and 126 as a result of encountering the particle stream in the chamber 120, the portion 124 results from particle scattering reflection action while the portion 126 results from passage through the particle stream. The energy portion 126 is passed through the window aperture structure 128 to a laser intensity monitor device 130 that provides an electrical signal representing the instantaneous amplitude of the energy portion 126. The laser intensity monitor device 130 provides an electrical output signal which is called a transmission measurement signal and indentified with the number 131 in FIG. 1A. The transmission measurement signal can be combined with other electrical signals generated from the FIG. 1A apparatus for determining the nature of particles in the window region 119 of the chamber 120, as is described below.

The energy portion 124 in FIG. 1A, which results from scattering action of the particles in window region 119, is conducted through an optical processing system shown in FIG. 1A and also shown with additional detail in FIG. 1B of the drawings. In the FIG. 1A apparatus, the plane which is defined by the center line of the energy portion 124 and the path 116 is identified as the scattering plane, while the angle 121 within the scattering plane is called the scattering angle.

The size of the particles being considered in the FIG. 1A appaatus influences selection of both the desired operating wavelegfth of the laser 102, and the scattering angle 121 at which the largest difference between orthogonal polarization states of the scattering energy 124 is to be found. In accordance with these relationships, the above-indicated 308 nanometer wavelength for the output energy of the laser 102 is found to be optimum for particle sizes which are in the micron and submicron range and location of the scatter light receiving optics at a scattering angle 121 in the range of 90° has been found optimum. In determining the operating spectrum of the laser 102, it is found desirable to employ a principal optical wavelength which is no larger than three times the diameter of the smallest particle of interest. The ability to tune the laser 102 and thereby optimize the relationship between optical energy wavelength and particle size to at least some degree is therefore found desirable. The above-identified excimer laser provides a limited degree of output energy tuning capability which is desirable for this use.

The particle scattered optical energy 124 may be considered to have two polarization components, one parallel to the scattering plane and another perpendicular to the scattering plane. These two components are segregated in the polarizer beamsplitter 142 in the optical processing system in order that the relative magnitude of each component portion 124 can be separately measured for each particle sample in the window region 119.

The optical processing of the energy portion 124 as shown in FIG. 1A includes the transmission of this energy through the window aperture structure 134 to a collection lens 136. The lens 136 images the window area 119 onto an optical slit which is shown at 138. The images within the slit 138 are collimated by a collimation lens 140 for passage through the polarizer beamsplitter 142. One output signal from the polarizer beamsplitter 142 is imaged on the input surface of an image intensifier 170 by an imaging lens 154 with a background rejection filter 168 being interposed between the imaging lens 154 and the image intensifier input surface. The output surface of the image intensifier 170 is imaged on the input face of a cryogenically-cooled vidicon 174 by a relay lens 172 which is located between the image intensifier 170 and the vidicon 174. Other imaging array detectors such as a Reticon ™ or charge coupled device (CCD) could be substituted for the image intensifier-vidicon conbination.

Additional details of the optical elements located between the particle chamber window aperture structure 134 and the vidicon 174 are shown in FIG. 1B. FIG. 1B represents a side view of the FIG. 1A apparatus showing parts which are located behind the above-recited parts in the FIG. 1A view. In FIG. 1B the collection lens 136, slit 138, collimation lens 140, polarizing beamsplitter 142, imaging lens 154, and background rejection filter 168 that were shown in FIG. 1A are repeated in somewhat enlarged form and are accompanied by the optical elements used in processing the second output signal from the polarizing beamsplitter 142.

The two outputs of the polarizing beamsplitter are indicated at 146 and 148 in FIG. 1B, the output 148 being polarized in one direction as is indicated by the arrow 152, and the output 146 being polarized in an orthogonal direction, as indicated by the symbol 150.

The optical signal 148 results from transmission of collimated energy form the lens 140 through a beamsplitting mirror apparatus while the output 146 results from reflection of energy from the beamsplitting mirror apparatus 144. The beamsplitter outputs 146 and 148 represent the orthogonally polarized components of the scattering energy portion 124, that is, the components which are parallel to the scattering plane and perpendicular to the scattering plane.

According to the theory of scattering as defined by Gustav Mie, and others, as the size of the particles causing the scattering decreases below the wavelength of the incident light, the scattered light component which is parallel to the scattering plane will diminish in amplitude when observed at a 90° scattering angle and allow the light component which is perpendicular to the scattering plane to become predominant. According to this phenomenon, if the FIG. 1A and 1B apparatus is arranged to make the perpendicular and parallel components approximately equal in magnitude, there results a very sensitive measurement of particle size; that is, as soon as the particle size departs from the size providing equal parallel and perpendicular polarization components, one of these components will quickly become dominant. If the particle size grows, the signal 146 for example, representing the polarized component parallel to the scattering plane, will become dominant.

Use of this phenomenon to determine particle size, number densities and distributions consequently involves measurement of the relative magnitudes of signal components 146 and 148 for each of the flow locations that are of interest within the window region 119. The apparatus shown in FIG. 1B enables this measurement of relative magnitude by presenting a pair of physically segregatable images to the image intensifier and vidicon 170 and 174. These two physically segregatable images are indicated at 164 and 166 in FIG. 1B.

The optical processing elements for the image 166 were described in connection with FIG. 1A above. The optical processing elements for the image 164 include the three mirrors 158, 160 and 162, which serve to displace and properly orient the image 164, and the imaging lens 156 which corresponds to the imaging lens 154 used with the image 166. The appearance of the images 164 and 166 on the input surface of the image intensifier 170 or at the vidicon 174 is indicated at 304 and 306, respectively, in FIG. 3 of the drawings. These images and other details of the FIG. 3 drawing are described below.

The FIG. 1A and 1B apparatus therefore optically accomplishes a mapping of the flow cross-section window area 119 onto the receiving face of an optical-to-electrical transducing device such as the vidicon 174. (The vidicon 174 may be used alone or in combination with an image intensifier 170 preceding the vidicon receiving face when required by the optical signal levels.) This mapping is in the form of two physically separated and distinguishable images each representative of an orthogonal polarization component of the scattered light received from the particle flow cross-sectional window. The number of particle diagnostic locations obtained from the mapped window area images, the images 164 and 166 in FIG. 1B, is determined by the elected scanning pattern and the resolution capability of both the optics and the optical-to-electrical transducer apparatus and also upon the capability of the accompanying electronic processing circuits.

The software which controls data acquisition in the described embodiment of the invention permits dividing the mapped region of the receiving face into a maximum number of 32 zones. Improved software would permit a number of zones limited only by the resolution of the detector used as the optical-to-electrical transducing device. Thus, the described embodiment of the invention permits particle diagnostics measurements to be made simultaneously within up to 32 separate zones of the window area 119. Each of these zones is represented in the two different images 164 and 166, and therefore, data storage corresponding to twice the number of measurement zones employed is required. The amount of data stored for each vidicon can, assuming digital acquisition and storage is employed, depend upon the width of the slit 138 and the degree of resolution desired. In one embodiment of the invention, the number of data bytes stored for each scan is 13,312 (or 106,496 bits).

Returning now to the FIG. 1A drawing, the images indicated at 164 and 166 in FIG. 1B are received on the imput or active surface of image intensifier 170 which serves to amplify or increase the intensity of these images while also maintaining a favorable signal-to-noise ratio during this amplification. The intensifier 170 represents an image of similar configuration and increased intensity variations on an output surface for use by a scanning optical-to-electrical transducer such as the vidicon 174.

Image intensifier devices are well-known in the optical and electrical signal processing art and are available as commercial items. An image intensifier indentified as a dual stage device manufactured by ITT Electro Optics Div. of Fort Wayne, IN is suitable for use in the FIG. 1A and 1B apparatus. This image intensifier, although suitable for use in the FIG. 1A and 1B apparatus, is actually not optimally matched as to spectral response with the spectrum of the scattered energy 124 and the optimum sensitivity of the preferred vidicon tube. A modification of the image intensifier through the use of fluorescent coatings over the intensifier surfaces or other techniques could be employed to more optimally match these respective response spectra, however, the acceptance of a less than perfect match between the input spectra without resorting to fluorescent coatings or other adaptations has been found satisfactory.

The rejection filter 168 which is located just ahead of the image intensifier receiving surface serves to transmit the laser wavelength of 308 nanometers and reject other wavelengths, especially visible light.

The optical-to-electrical transducer device preferred for use in the FIG. 1A and 1B apparatus includes scanning ability, that is, the ability to select which of the pixels received on the receiving face or image plane is to be transduced into an electrical signal at any given time. This selectivity of course enables the flow location selectivity capability included in the present invention. Devices of this nature are commonly employed in television cameras and other electronic scanning uses, and include the image orthicon, the previously implied vidicon vacuum tube and various solid state scanning devices. For the present apparatus a type GEZ7975A vidicon camera tube which is manufactured by General Electric Company of Syracuse, NY has been found satisfactory—when arranged to receive cryogenic low temperature cooling in order to maintain adequate signal-to-noise ratio.

In the FIG. 1A and 1B apparatus it has been found satisfactory to operate this vidicon at a temperature of $-40°$ C. in order to achieve a desirable spectral response. Operation at this temperature may be achieved by surrounding the vidicon by a closed, heat loss restricted, cooling chamber and supplying a liquified refrigerant gas such as nitrogen to the vidicon surroundings. Such cooling arrangements for the vidicon are indicated at 200 and 201 in FIG. 2 of the drawings. Similar or other cooling arrangements may be needed with the solid state and alternate optical-to-electrical transducer devices indicated herein—depending upon signal and transducer characteristics.

FIG. 3 of the drawings shows how the images formed at 164 and 166 in FIG. 1A and 1B actually appear on the input or output surfaces of the image intensifier 170 and also how these images would appear on the receiving face transducer surface of the cooled vidicon 174 through the use of the relay lens 172. In FIG. 3, an image plane representing for example, the output surface of the image intensifier 170, is shown at 300 and the mapping of the slit 138 onto the transducer surface of the vidicon is indicated at 302. The images formed at 164 and 166 on the image intensifier in FIG. 1 are indicated at 304 and 306, respectively in FIG. 3, as they appear on the vidicon transducer surface.

The images 304 and 306 are shown as uniformly shaded shadows in FIG. 3 for the sake of drawing convenience. Actually, variations in image intensity or amplitude are encountered across both the long and short dimensions of each of the images 304 and 306. The intensity variations along the long dimension of the images relate to positions within the illuminated window in the chamber 120 while intensity variations along the short image dimension relate to the scattering signal components. The area under the short dimension intensity variation curves is, of course, the desired signal from scanning the FIG. 3 images. A pair of typical intensity variation curves might be obtained from one of the scan trajectories 308–314 in FIG. 3 is shown in FIG. 4 of the drawings. In the FIG. 4 intensity variation curves the amplitude and area under the parallel polarization curve 400 is shown to be larger than under the perpendicular polarization curve 402. In a FIG. 3 type of image presentation the image represented by the curve 402 would be less intense, and depending upon the elected "threshold" of the drawing shading, smaller in the short dimension than that of the curve 400.

Each of the flow positions in the window 119 of FIG. 1A is mapped into a region of the vidicon transducer surface represented by four adjacent rows of pixels. The numbers 308, 310, 312, and 314 of FIG. 3 indicate four adjacent scan paths in one of the two orthogonally polarized images of one sample volume in the flow field. In the described embodiment of the invention, the electrical signals from each pixel in the scan paths 308, 310, 312 and 314 are digitized by interface 220 and averaged in the digital computer 230, in order to obtain adequate signal-to-noise ratio. The resultant function is a digitized profile of the convolution of the slit 138 with each of the two orthogonally polarized images of the flow window 119. Depending upon the scanning resolution achievable in the vidicon 174, the resolution and image size limitations of the optical elements in FIG. 1A and 1B, and the desired number of flow positions to be located in the window 119, the number of scan lines averaged for each flow position can be adjusted either up or down from the indicated number of four. Groups of scanning lines for two other flow positions are indicated at 320 and 322 in FIG. 3. In addition to the three groups of scanning lines shown in FIG. 3, additional groups of scanning lines which are omitted in FIG. 3 for the sake of drawing clarity could be present. In the described embodiment of the invention, the slit-defined flow image is resolved into thirty-two positions or zones, since the data acquisition software used permits a maximum number of thirty-two zones. Improved software and a different optical-to-electrical transducer would permit spatial resolution of more than thirty-two zones within the window 119 of FIG. 2.

An electrical system interconnected with the optical apparatus of FIG. 1A and 1B is shown in FIG. 2 of the drawings, along with certain elements of FIG. 1A and 1B which are also repeated in FIG. 2 for reference and interconnection explanation purposes. The FIG. 2 apparatus includes power supplies for the vidicon 174, the image intensifier 170, and the laser 102. These power supplies are shown at 210, 234, and 242 in FIG. 2. The vidicon power supply is also shown as an assembly 210 which also incorporates a scanning or deflection drive apparatus which determines the instantaneous location of the optical-to-electrical transducing agent (vidicon electron beam) on the target array of the vidicon 174. The vidicon electron beam deflection signals are coupled between the power supply 210 and the vidicon 174 by way of the indicated paths 204 and 206. A filament control signal 252 is is required for low signal-to-noise applications. The power supply 210 also includes a readout gate signal which is coupled on the path 202. The image intensifier power supply 234 is coupled with the image intensifier 170 by way of a high voltage connection 248 and a gating signal 250. The laser power supply 242 is arranged to pulse the laser 102 at a rate of approximately 100 times per second. Such pulsing is initiated by a trigger from the computer 230 along the path 246 to generate the 20 nanoseond pulse of the excimer laser device.

Overall operation of the FIG. 1A, FIG. 1B, and FIG. 2 apparatus can be controlled with the use of a digital minicomputer as is represented at 230 in FIG. 2. Although any digital computer allowing real time data acquisition and control is acceptable, for this use the PDP-8 computer manufactured by Digital Equipment Corp., of Maynard MA, has been found desirable for accomplishing control of the described apparatus. Use of an LSI-11 computer (manufactured by the same company) would permit even greater apparatus flexibilty. One example of software capable of operating and collecting data from systems of the FIG. 2 type is described in the academic thesis "Software Techniques for the Acquisition of Optical Data from a Minicomputer-Based Image Intensifier-Vidicon System" written by John H. Jones in 1979 for a Master of Science Degree program at the University of Tennessee, Knoxville TN. The disclosure of the Jones thesis is hereby incorporated by reference herein. Other software appropriate to this task can be prepared by persons skilled in the compute art from the description herein and from known characteristics of components in the FIG. 2 system. Software of this type can also be purchased as an item of commerce.

Some functions of the computer 230 may alternately be replaced by additional dedicated electronic hardware located in block 220, and designed to sequence and control operation of the optical elements, interface systems, and related data acquisition and signal storage elements according to the descriptions herein provided and in accordance with the known operating characteristics of such elements. Operations of the image intensifier/vidicon system by the computer 230 for example, involves principally the activation of vidicon electron beam supply filaments and intensifier electron accelerating potentials at appropriate times prior to use of the system. Intensifier accelerating potential control and intensifier gating are achieved by signals along the path 236. A vidicon-computer interface circuit is indicated at 220 in FIG. 2 and is used for the purpose of communicating the analog and digital signals existing at the computer output and input buses 222 and 224 with the power supply 210 and the vidicon 174. The vidicon output signal is shown at 208 connected with the interface circuit 220. The interface circuit 220 may also include latching device memory circuits frequently encountered in controllers—for the purpose of freeing the computer output and input buses 222 and 224 from the need for full-time connection with the vidicon and its power supply signals.

The laser control circuits 244 provide the control and simple timing capability needed to initiate and terminate laser operation in response to brief signals received on the path 246 from the computer 230. The laser and image optical systems 107 and 176 in FIG. 2 are the optical systems described in connection with FIGS. 1A and 1B above. The scattering probe volume block 240 in FIG. 2 represents the particle flow volume contained within the area of the window 119 in FIG. 1A.

Electrical data signals representing portions of the images 304 and 306 in FIG. 3 are transmitted as analog signals along the path 208 to the interface circuits 220 for analog-to-digital conversion and then transferred to the computer 230 along path 224 and ultimately stored in a data storage apparatus 232 which may take the form of a floppy disk, magnetic tape, or other data storage arrangements as are known in the art. The data stored in the apparatus 232 may, of course, be processed or reduced in an off-line fashion using a larger and more sophisticated general purpose computer which is programmed to accomplish the tasks of further data reduction and final particle size and density analysis. Alternately, a mini-computer or microcomputer of sufficient memory size and speed to be compatible with the requirements of the data analysis software may be dedicated to the purpose of final data analysis.

Equations defining a possible arrangement of the data analysis to be performed on the vidicon signals are shown in the report "Selected Results from an Experiment Venting an $H_2O$ Jet into a High Vacuum", AEDC TR-84-28 dated January 1985 and published by the Arnold Engineering Development Center, Arnold AFS, TN. The AEDC TR-84-28 report is available to qualified organizations from the Defense Technical Information Center and is hereby incorporated by reference herein. The AEDC TR-84-28 report also discloses additional details of a system of the FIG. 2 type and describes a use example of such a system.

A copy of a computer program listing based on the TR-84-28 relationships and determining the average particle diameter and particle number density in each of a number of specified spatial zones from experimental values of Mie scattering data, transmission data and pre-generated computer files of theoretical Mie scattering functions for the fuel vent example in TR-84-28 is included in the appendix of this specification. A second computer program listing for generating such theoretical Mie scattering files is also included in the appendix: this second program is based on the concepts involved in a program accepted in the Hewlett-Packard Corporation user's library on Sept. 5, 1978 and catalogued as HP library number 027560 in the HP 67/97 user's library.

The vidicon signals 208 are also coupled in the interface circuitry 220 to a storage oscilloscope 216 along with suitable x-y drive signals from the interface 220 using the paths 212 and 214 respectively. The storage oscilloscope 216 is found convenient for monitoring the operation of the FIG. 1A, FIG. 1B, and FIG. 2 apparatus, particularly with respect to making preliminary adjustments and alignments and monitoring the scatter signals originating in different portions of the stream window 119.

Returning now to the FIG. 2 diagram, the X-Y position signals 212 and 214 are also coupled in the interface 220. After processing by the computer 230, the vidicon signal can be coupled to the Y-axis of the storage oscilloscope 216 after digital-to-analog conversion in interface 220. X and Y position data for this storage is supplied as indicated between the interface 220 and the oscilloscope 216. The storage oscilloscope 216 is found to be convenient for monitoring operation of the FIG. 1A, FIG. 1B, and FIG. 2 apparatus, particularly with respect to making preliminary adjustments and alignments and monitoring the scattering signals originating in different portions of the scattering volume 119 and also provides a display of the intensity of the scattering signals versus position along the slit axis. The oscilloscope can also be used as a slow scan TV monitor during the making of preliminary optical adjustments.

The use of computer control for the FIG. 1 and FIG. 2 apparatus allows considerable flexibility in the manner of generating and collecting the scatter signal data. For example, as was indicated above, an arrangement wherein the output of each line of pixels of the polarization component images is averaged with a plurality of adjacent pixels, such as for the indicated four scan trajectories 308, 310, 312 and 314 in FIG. 3, has been found desirable but can be easily modified as to the number of scan trajectories included in the average. Since the initiation of vidicon scans and the location of the scan trajectories are controllable from the computer 230, a modification of the four lines per zone arrangement and a corresponding modification of the data collection and storage arrangement can in fact be achieved by a change of input parameters from a computer keyboard.

The FIG. 1 and FIG. 2 apparatus may be considered a modification of a molecular scattering measurement apparatus of the Raman scattering or Rayleigh scattering types. Such apparatus is often used to determine gas temperature and density in flows, from the intensity variation and angular variation characteristics normally considered in molecular scattering measurements. In the present invention the extraction of polarization measurement information at the plural simultaneously measured positions in the window 119 in FIG. 1A makes possible the determination of particle average size and number density information at a plurality of locations in particle-laden flows.

The described apparatus may be considered to be an imaging device, that is, apparatus capable of measuring information from more than one point in a particle flow at one time and in the manner of a camera—an apparatus wherein positions in a particle flow are mapped into positions on a retina; the use of beam splitting polarized component techniques in such imaging devices as disclosed herein significantly enhances the capability of the achieved particle diagnosis.

In the described apparatus, particle size information is obtained from the difference in the optical energy existing in two polarization states, that is, from the ratio of the signal amplitude in two polarization states. In performing Mie scattering measurements the size parameter, which is equal to the ratio of the particle circumference and the illumination wavelength, should be kept within a defined range of values in order to optimize the degree of polarization of the scatter signal obtained; variation of the illuminating light wavelength provides a tool by which size parameter can be maintained within the desired range. For measuring small particles the size of the scattering angle as was defined in connection with FIG. 1A above, is somewhat sensitive and is believed to be optimum at the indicated 90° value.

Information regarding the density of the particles in the stream being measured is obtained from the combination of the two segregated polarization components measured at the vidicon and the straight through signal which passes through the moving particle stream, i.e., the signals 124 and 126 in FIG. 1A, in accordance with a predetermined relationship. The particle density measurement algorithm in particular needs to have the capability of distinguishing the presence of many particles of small size from the presence of few particles of large size. The described apparatus includes four pieces of information for achieving this distinction, the incident laser intensity, the particle transmitted intensity, the scatter signal in one polarization state and the scatter signal in the orthogonally polarized state.

It may be noted in the above description of the FIG. 1A and FIG. 1B apparatus that no mention is made of measurements at different elevations within the window 119, that is, at different focus distances for the collection lens 136. In practice it is found desirable in making such different elevation measurements to re-orient the particle stream in higher or lower elevations within the chamber 120 in preference to changing the focal point of the lens 136 and attempting to vary the elevation in the stream illuminated by the laser energy received through the lens 110, especially since angular tilting of the path 116 would introduce complexities into the achieved results.

The particle size measurements achieved by the described apparatus, that is, the indicated average particle size, is found to be of relatively large moment, that is, in the range of the fifteenth or twentieth moment or the fifteenth to twentieth root to the integral of the product of the fifteenth to twentieth power of particle size with the particle size distribution function; this arrangement is desirable in providing a high degree of sensitivity as to the maximum particle size.

In processing the data signals obtained from the vidicon 174, that is, the signals stored in the apparatus 232 in FIG. 2 it is desirable to perform an integration of instantaneous signal intensity over the width of the slit 138 and use this integrated value to represent particle scattered light energy. This integration procedure reduces concern with intensity variations across the dimensions of the illuminating energy slit 138 as inherently occur in a laser device. In connection with performing this integration step, it is found necessary to subtract a baseline value which is obtained by integration over the non-imaged portion of the intensity profile obtained from the vidicon transducer surface.

A portion of the processing following data storage on device 232 also includes a Mie scattering calculation, in order to determine the range of particle sizes within which experimental data and calculations agree. Such a calculation is used to predict the intensity to be expected at a given scattering angle with a given excitation wavelength, a given particle size and polarization state. The Mie scattering calculation enables regression of the upper and lower limits on the average particle size at a given spatial location.

The described apparatus and other embodiments of the invention can be used in a variety of particles scattering measurement situations, including the analysis of particles in a fuel and air mixture preceding a combustion device, in air pollution and dust particle analysis—such as might be desirable in an industrial clean room, a surgical suite, or for atmospheric measurements. Other uses include the measurement of biological particles, (i.e., pollen, spores, and bacteria clusters) in a moving stream. The apparatus may be arranged to be portable in nature in order that transport to the site of the particle stream is conveniently accomplished.

While the apparatus and method herein described constitute a preferred embodiment of the invention, it is to be understood that the invention is not limited to this precise form of apparatus or method, and that changes may be made therein without departing from the scope of the invention, which is defined in the appended claims.

We claim:

1. Particle stream diagnostic apparatus comprising:
   means for illuminating a cross-section of said particle stream with polarized coherent light directed along a lateral axis traversing said stream and cross-section;
   means for generating a first electrical signal representing light flux from said illuminating means transmitted across said cross-section through said particle stream;
   means located at a predetermined scattering angle with respect to the plane of said cross-section lateral axis and said stream for collecting particle scattered light originating in multiple locations of said illuminated cross-section as first light signals;
   means for segregating said first light signals into component second and third signals of dissimilar polarization angles;
   means for segregating said second and third light signals over an image plane, each said image plane light signal including geometrically identifiable signal areas originating respectively in light form said cross-section multiple locations;
   means for transducing said signal areas in said second and third light signals on said image plane into second and third electrical signal pairs; and
   means for analyzing a plurality of said first, second and third electrical signals.

2. The diagnostic apparatus of claim 1 wherein said means for illuminating includes a laser.

3. The diagnostic apparatus of claim 2 wherein said laser is a pulsed laser.

4. The diagnostic apparatus of claim 3 wherein said laser is a pulsed excimer laser.

5. The diagnostic apparatus of claim 3 wherein said laser is a frequency doubled ruby laser.

6. The diagnositc apparatus of claim 3 wherein said laser is a frequency quadrupled YAG laser.

7. The diagnostic apparatus of claim 2 wherein said laser has a major output spectrum selected in response to the upper and lower limits of particle size in said particle stream.

8. The diagnostic apparatus of claim 2 wherein said laser has a major output spectrum in the range of two hundred seventy-five to three hundred thirty nanometers.

9. The diagnostic apparatus of claim 2 wherein said laser has a vertically polarized majority output.

10. The diagnostic apparatus of claim 9 wherein said laser has a vertical polarization amplitude to horizontal polarization amplitude ratio of at least thirty-five to one.

11. The diagnostic apparatus of claim 2 further including polarization means located in the light output path of said laser intermediate to said laser and said particle stream for increasing the vertical to horizontal polarization ratio, in a plane parallel to the plane of said particle scattered light, of the illumination received at said particle stream.

12. The diagnostic apparatus of claim 11 wherein said polarization means includes an external polarizing element.

13. The diagnostic apparatus of claim 12 wherein said polarization means includes a plurality of quartz windows mounted at Brewster's angle rotational positions.

14. The diagnostic apparatus of claim 2 wherein said laser is tunable over spectral regions adjacent a nominal output wavelength.

15. The diagnostic apparatus of claim 2 wherein said means for illuminating includes a focusing lens located intermediate said laser and said particle stream.

16. The diagnostic apparatus of claim 15 wherein said scattering angle is in the range of eighty-five to ninety-five degrees.

17. The diagnostic apparatus of claim 1 wherein said scattering angle is in the range of eighty-nine to ninety-one degrees.

18. The diagnostic apparatus of claim 17 wherein said scattering angle is ninety degrees.

19. The diagnostic apparatus of claim 1 wherein said multiple locations are greater than ten in number.

20. The apparatus of claim 1 wherein said means for segregating said first light signals ihto component signals includes an optical beam splitter.

21. The apparatus of claim 20 wherein said means for dispersing includes a mirror member located in at least one output path of said optical beam splitter.

22. The apparatus of claim 1 wherein said image plane is a portion of a light intensifier apparatus.

23. The apparatus of claim 1 wherein said image plane is the photosensitive surface of an optical-to-electrical transducer element.

24. The apparatus of claim 23 further including refrigeration means for cooling said optical-to-electrical transducer element to temperatures below ambient, whereby thermal noise components in the output signal of said transducer element are reduced in magnitude.

25. The apparatus of claim 1 wherein said means for transducing includes a vidicon tube.

26. The apparatus of claim 1 wherein said means for transducing includes a solid state optical-to-electrical transducer element.

27. The apparatus of claim 26 wherein said transducer element is a charge coupled device transducer.

28. The apparatus of claim 1 wherein said means for analyzing includes a digital computer connected and programmed to collect and store successive values of said first, second and third electrical signals in organized arrangement.

29. The apparatus of claim 1 wherein said means for analyzing includes means for comparing the relative magnitude of said second and third light signals.

30. A method for particle stream scattering diagnosis comprising the steps of:
   illuminating a cross-section of said particle stream with polarized coherent light directed along a lateral axis transversing said stream and cross-section;
   generating a first electrical signal representing light transmitted across said cross-section through said particle stream;
   collecting particle scattered light originating in multiple locations within said cross-section and directed at a predetermined scattering angle with respect to the plane of said cross-section lateral axis and said stream into first light signals;
   segregating said first light signals into component second and third signals of dissimilar polarization;
   mapping said second and third light signals onto an image plane, each said image plane light signal including geometrically identifiable signal areas originating respectively in light from said cross-section and multiple locations;
   transducing said signal areas in said second and third light signals on said image plane into second and third electrical signals; and
   analyzing a plurality of said first, second and third electrical signals for particle population related variations.

31. The method of claim 30 further including the step of tuning the wavelength of said polarized coherent light to an optimum wavelength with respect to the size of said scattered particles.

32. The method of claim 30 wherein said step of transducing includes scanning said image plane.

33. The method of claim 30 wherein said analyzing step includes performing a Mie scattering theory based analysis.

34. Particle stream diagnostic signal generating apparatus comprising:
   laser means for illuminating a cross-section of said particle stream with coherent polarized light directed along an axis transverse of said cross section;
   means located at a predetermined angle with respect to said cross section axis and said stream for collecting the particle scattered light originating in plural locations of said illuminated cross section into first optical signals;
   means for segregating said first light signals into a second and third signal pair of component optical signals of orthogonal polarization vectors;
   means for projecting said second and third component optical signals over a common image plane, said image plane receiving a second and third optical signal pair for each said cross-section location first optical signal; and
   means for transducing said second and third optical signal pairs into electrical signal pairs.

35. The apparatus of claim 34 wherein said projected second and third component optical signals are side by side physically disposed on said image plane.

* * * * *

UNITED STATES PATENT AND TRADEMARK OFFICE
CERTIFICATE OF CORRECTION

PATENT NO. : 4,679,939

DATED : July 14, 1987

INVENTOR(S) : Bill P. Curry et al

It is certified that error appears in the above-identified patent and that said Letters Patent is hereby corrected as shown below:

```
Col 1, line 11, "distibution" should be --distribution--.
Col 5, line 63, "appaatus" should be --apparatus--.
Col 6, line 43, "conbination" should be --combination--.
Col 6, line 63, "form" should be --from--.
Col 10, line 52, "compute" should be --computer--.
Col 10, line 63, "Operations" should be --Operation--.
Col 13, line 43, "to"  (second occurrence) should be -- of --.
Col 14, line 4, "particles" should be --particle--.
Claim 1, line 21, "form" should be --from--.
Claim 20, line 2, "ihto" should be --into--.
Claim 34, line 55, "over a common" should be --onto an--.
```

Signed and Sealed this

First Day of March, 1988

*Attest:*

DONALD J. QUIGG

*Attesting Officer*  *Commissioner of Patents and Trademarks*